United States Patent
Quinn et al.

(10) Patent No.: US 9,295,782 B2
(45) Date of Patent: Mar. 29, 2016

(54) MULTIPLE USE DISPOSABLE INJECTION PEN

(75) Inventors: Michael Quinn, East Hanover, NJ (US); Richard Cronenberg, Mahwah, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 14/385,141

(22) PCT Filed: Mar. 15, 2012

(86) PCT No.: PCT/US2012/029306
§ 371 (c)(1), (2), (4) Date: Dec. 24, 2014

(87) PCT Pub. No.: WO2013/137893
PCT Pub. Date: Sep. 19, 2013

(65) Prior Publication Data
US 2015/0112274 A1    Apr. 23, 2015

(51) Int. Cl.
*A61M 5/00* (2006.01)
*A61M 5/315* (2006.01)

(52) U.S. Cl.
CPC ......... *A61M 5/31501* (2013.01); *A61M 5/3155* (2013.01); *A61M 5/31551* (2013.01); *A61M 5/31575* (2013.01); *A61M 5/31585* (2013.01); *A61M 5/31593* (2013.01); *A61M 5/31535* (2013.01); *A61M 5/31541* (2013.01); *A61M 5/31558* (2013.01); *A61M 2205/581* (2013.01); *A61M 2205/582* (2013.01)

(58) Field of Classification Search
CPC ................. A61M 2205/581; A61M 2205/582; A61M 5/31501; A61M 5/31535; A61M 5/31541; A61M 5/3155; A61M 5/31551; A61M 5/31558; A61M 5/31575; A61M 5/31585; A61M 5/31593; A61M 2205/58; A61M 2205/00; A61M 5/315; A61M 5/31533; A61M 5/31525; A61M 5/31526; A61M 5/31528; A61M 5/31545; A61M 5/31548; A61M 5/31556; A61M 5/31565; A61M 5/31566; A61M 5/31573; A61M 5/31576; A61M 5/31583; A61M 5/3159
USPC ........................................................ 604/207
See application file for complete search history.

(56) References Cited

U.S. PATENT DOCUMENTS

| | | | |
|---|---|---|---|
| 2004/0199117 A1* | 10/2004 | Giambattista et al. | 604/134 |
| 2007/0244436 A1* | 10/2007 | Saiki | 604/131 |
| 2008/0051713 A1 | 2/2008 | Kohlbrenner et al. | |
| 2010/0069845 A1* | 3/2010 | Marshall et al. | 604/135 |

FOREIGN PATENT DOCUMENTS

| | | |
|---|---|---|
| EP | 2351591 A1 | 8/2011 |
| WO | 2011068531 A1 | 6/2011 |
| WO | 2012125876 A1 | 9/2012 |

OTHER PUBLICATIONS

Notification of Transmittal of the International Search Report and the Written Opinion of the International Searching Authority, or the Declaration, Mailing Date Aug. 14, 2012, issued in International Application No. PCT/US2012/029306, 11 pages.

* cited by examiner

*Primary Examiner* — Jason Flick
(74) *Attorney, Agent, or Firm* — Dickinson Wright PLLC

(57) ABSTRACT

A medication injection pen (11) includes a housing (1) and a dose set knob (2) rotatable with respect to the housing (1). A brake assembly (68) is disposed in the housing (1) and has a ratchet member (43). A driver (21) includes at least one external tooth (57) engaging the ratchet member (43). The engagement between the ratchet member (43) and the at least one external tooth (57) substantially prevents the driver (21) from rotating with respect to the dose set knob (2) during dose setting and dose correcting. The engagement between the ratchet member (43) and the at least one external tooth (57) allows the driver (21) to rotate with the dose set knob (2) during an injection.

20 Claims, 21 Drawing Sheets

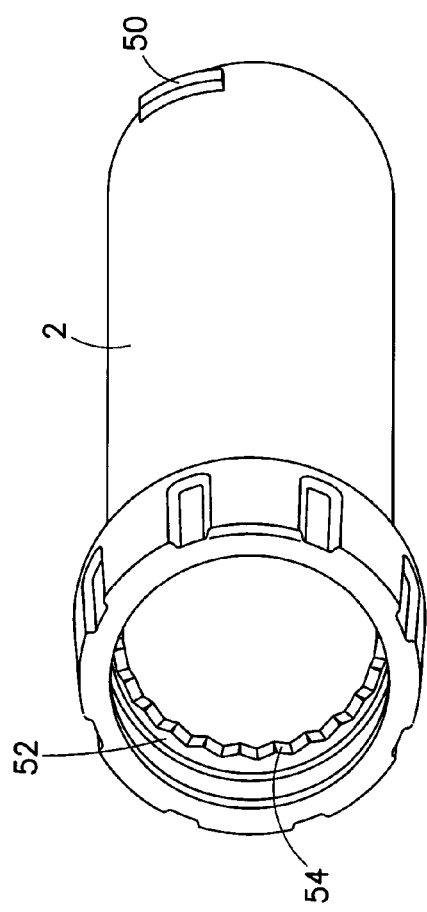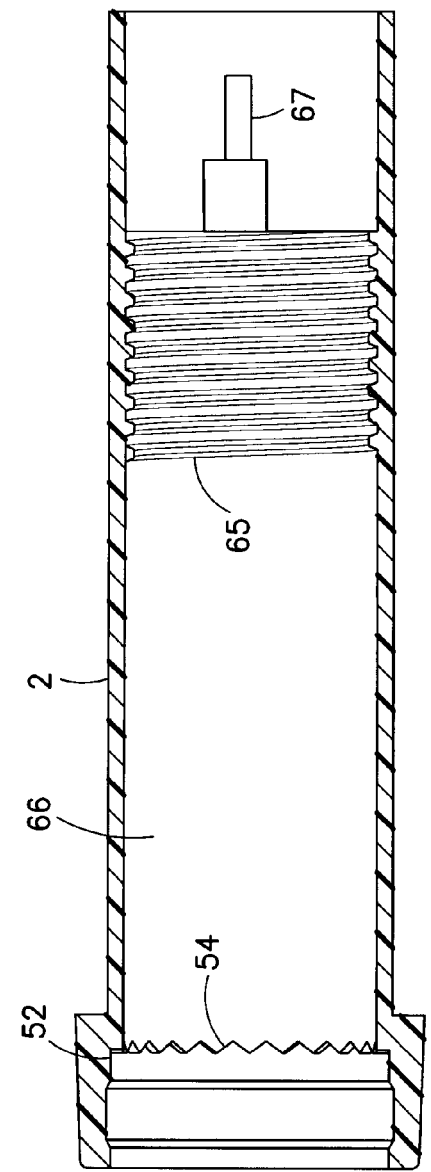

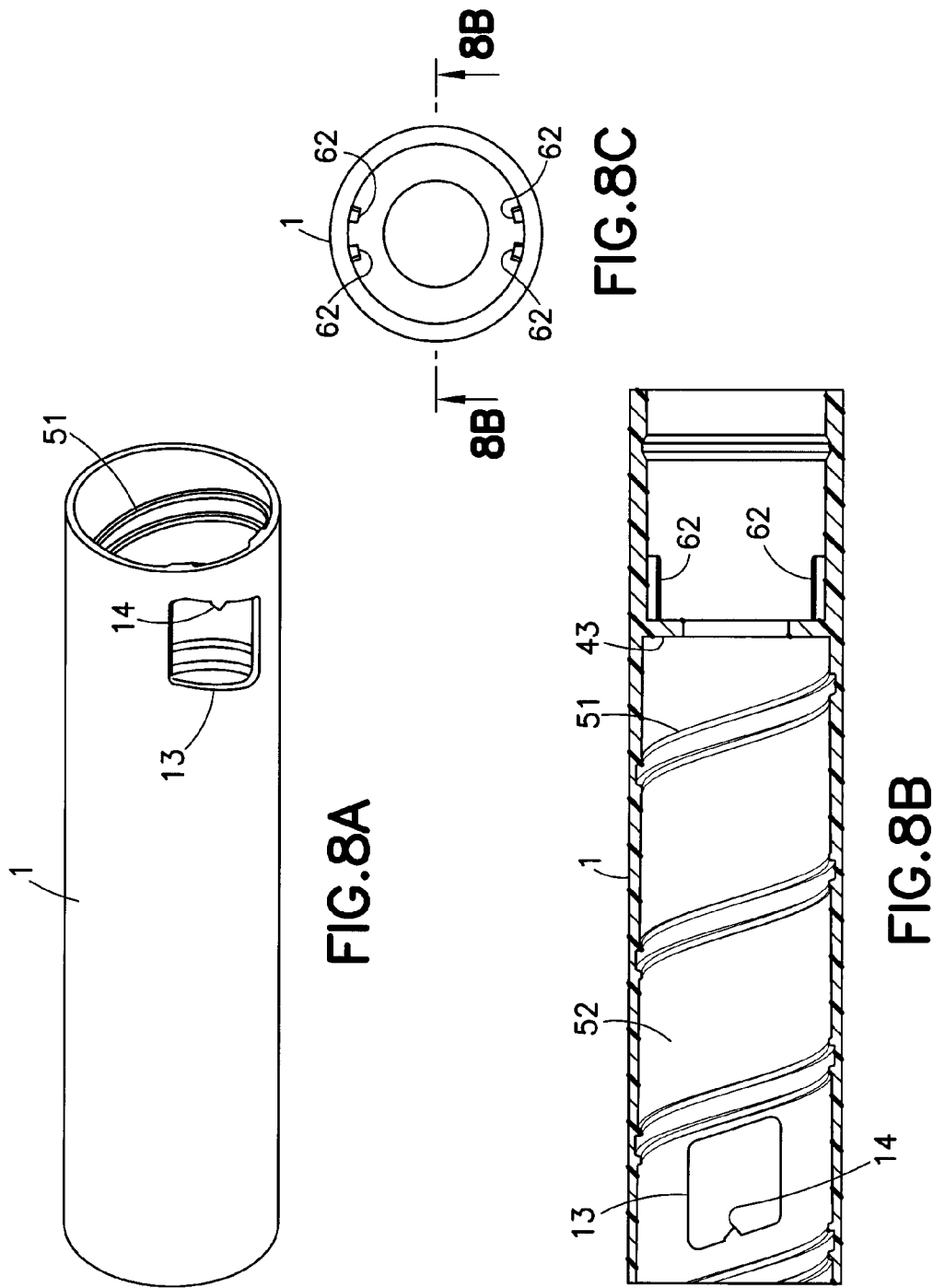

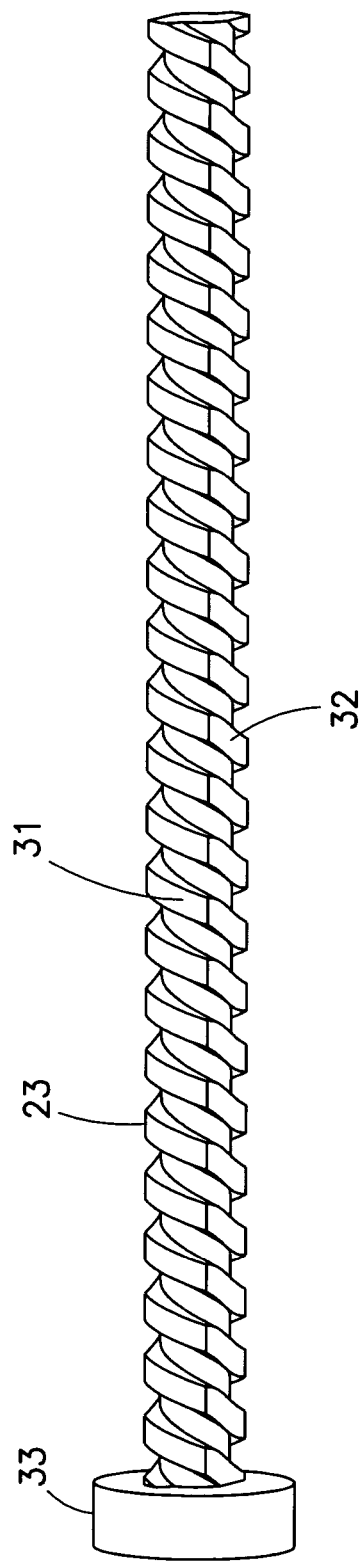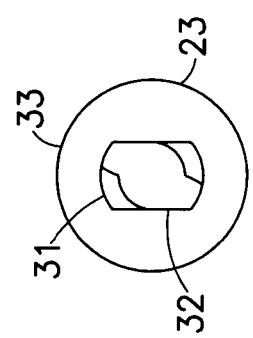

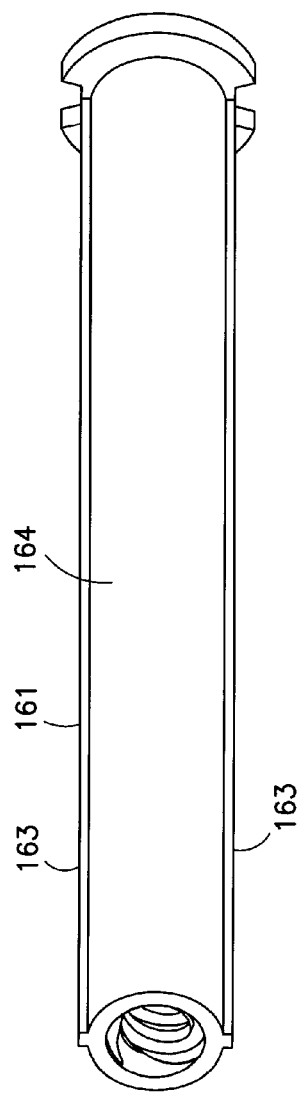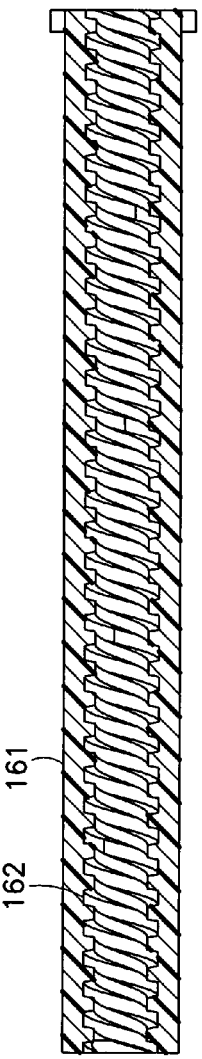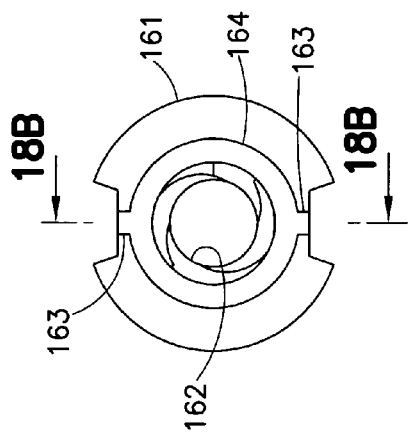

MULTIPLE USE DISPOSABLE INJECTION PEN

CROSS REFERENCE TO RELATED APPLICATIONS

This application is the U.S. national stage under 35 U.S.C. §371 of International Application No. PCT/US2012/029306, filed Mar. 15, 2012, the entire disclosure of which is hereby incorporated by reference.

FIELD OF THE INVENTION

The invention relates generally to a multiple use pen-type injection device. More particularly, the present invention relates to a multiple use pen-type injection device having means to prevent rotation of a driver when setting and correcting a dose.

BACKGROUND OF THE INVENTION

Various medication injection pen devices are known in the prior art. These prior art devices sometimes include features for enabling a user to correct a dose that has been set too large, which may be referred to as "dial back". Another feature that may be provided by some of the prior art devices is the ability to control a last dose of a medication cartridge such that a user cannot set a dose greater than the remaining amount of medication in the cartridge. This feature is sometimes referred to as last dose control or last dose management. Both of these features are desired by users of such pen devices; however, the prior art devices do not satisfactorily meet these needs. Many prior art devices may provide one of these features, but not both. Further, many of the prior art devices require additional steps for performing dial back, which are cumbersome and not intuitive to the user. Thus, there is a need in the art to provide improved functionality of dial back and last dose control mechanisms together in a medication injection pen.

Prior art pen injection devices commonly use driving components that are snap fit together to secure the components in place, thereby requiring tight manufacturing tolerances. Additionally, many prior art pen injection devices utilize one-way ratchet systems that are difficult for a user to access for customization. Such ratchet systems typically require a substantial and complex manufacturing process to accomplish. Accordingly, a need exists for a pen injection device that eliminates snap fitting components together to provide a simple assembly that is easily customizable.

SUMMARY OF EMBODIMENTS OF THE INVENTION

Exemplary embodiments of the present invention address at least the above problems and/or disadvantages and provide at least the advantages described below.

In accordance with an exemplary embodiment of the present invention, a medication injection pen includes a housing and a dose set knob rotatable with respect to the housing. A brake assembly is disposed in the housing has a ratchet member. A driver includes at least one external tooth engaging the ratchet member. The engagement between the ratchet member and the at least one external tooth substantially prevents the driver from rotating with respect to the dose set knob during dose setting and dose correcting. The engagement between the ratchet member and the at least one external tooth allows the driver to rotate with the dose set knob during an injection.

In accordance with another exemplary embodiment of the present invention, a medication injection pen includes a housing and a dose set knob rotatable with respect to the housing. A brake assembly is disposed in the housing and has a ratchet member. A brake tower includes at least one external tooth engaging the ratchet member. A lead screw is rotatable by rotation of the brake tower. A piston rod is axially movable by rotation of the lead screw to expel medication during an injection. The engagement between the ratchet member and the at least one external tooth substantially prevents the lead screw from rotating with respect to the dose set knob during dose setting and dose correcting. The engagement between the ratchet member and the at least one external tooth allows the lead screw to rotate with the dose set knob during an injection.

In accordance with another exemplary embodiment of the present invention, a medication injection pen includes a housing and a dose set knob rotatable with respect to the housing. A brake assembly is disposed in the housing and has a ratchet member. A brake tower includes at least one external tooth engaging the ratchet member. A lead screw is rotatable by rotation of the brake tower. A piston rod is axially movable by rotation of the lead screw to expel medication during an injection. The engagement between the ratchet member and the at least one external tooth substantially prevents the lead screw from rotating with respect to the dose set knob during dose setting and dose correcting. The engagement between the ratchet member and the at least one external tooth allows the lead screw to rotate with the dose set knob during an injection.

Additional objects, advantages and salient features of exemplary embodiments of the invention will become apparent to those skilled in the art from the following detailed description, which, taken in conjunction with annexed drawings, discloses exemplary embodiments of the invention.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings in which:

FIG. 7A is a perspective view of a dose set knob of FIG. 2;

FIG. 7B is an elevational view in cross-section of the dose set knob of FIG. 7A;

FIG. 8A is a perspective view of a pen upper body of the injection pen of FIG. 2;

FIG. 8B is an elevational view in cross-section of the pen upper body of FIG. 8A;

FIG. 8C is a distal end elevational view of the pen upper body of FIG. 8A;

FIG. 9A is a perspective view of a lead screw of the injection pen of FIG. 2;

FIG. 9B is a distal end elevational view of the lead screw of FIG. 9A;

FIG. 18A is a perspective view of a piston rod of the injection pen of FIG. 12;

FIG. 18B is an elevational view in cross section of the piston rod of FIG. 18A;

FIG. 18C is a proximal end elevational view of the piston rod of FIG. 18A;

Throughout the drawings, like reference numerals will be understood to refer to like elements, features and structures.

DETAILED DESCRIPTION OF EXEMPLARY EMBODIMENTS

The matters exemplified in this description are provided to assist in a comprehensive understanding of exemplary embodiments of the invention with reference to the accompanying drawing figures. Accordingly, those of ordinary skill in the art will recognize that various changes and modifications of the exemplary embodiments described herein can be made without departing from the scope and spirit of the claimed invention. Also, descriptions of well-known functions and constructions may be omitted for clarity and conciseness.

Figure 1:
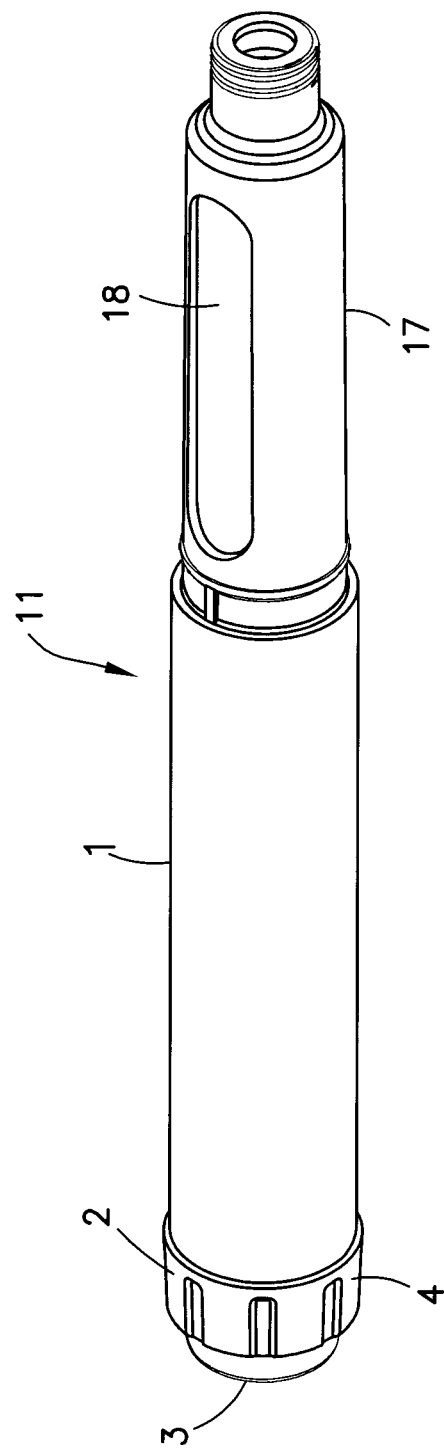
FIG. 1 is a perspective view of an injection pen according to a first exemplary embodiment of the present invention.
Figure 2:
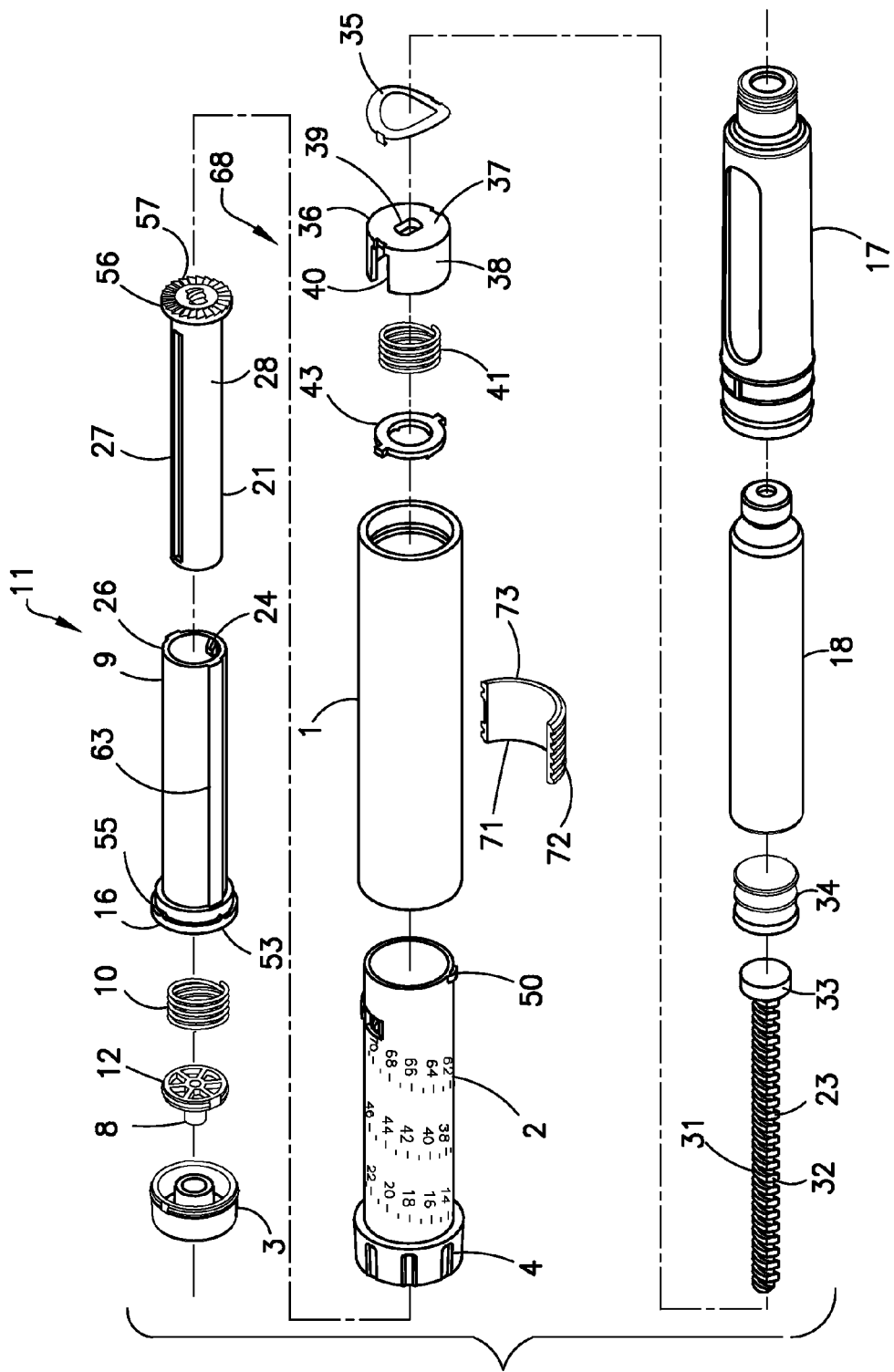
FIG. 2 is an exploded perspective view of the injection pen of FIG. 1.
Figure 3:
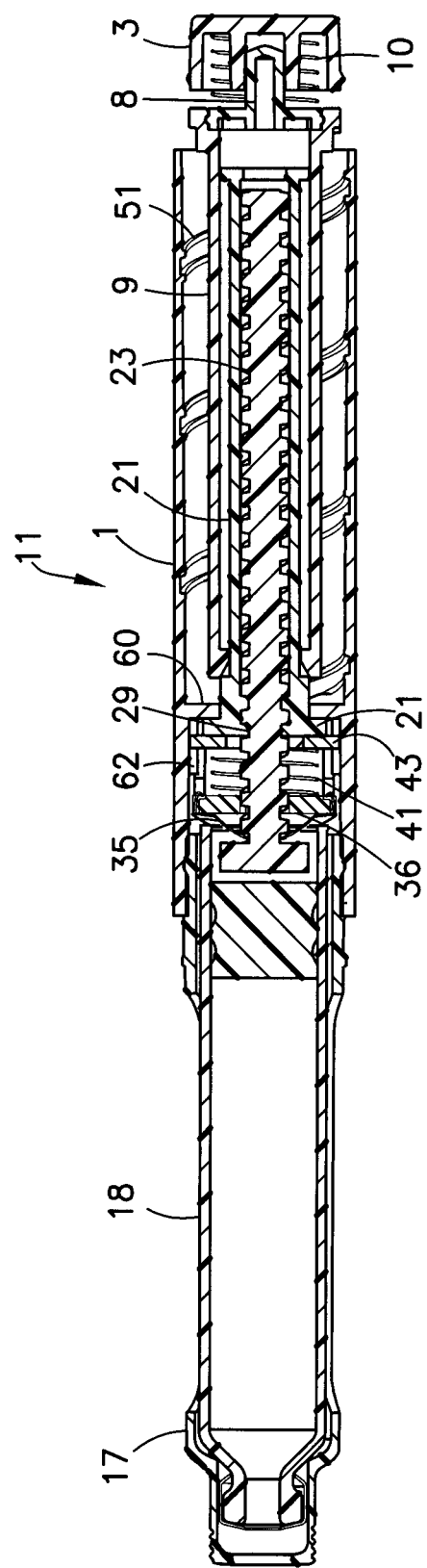
FIG. 3 is an elevational view in cross-section of the injection pen of FIG. 1 without a dose set knob for clarity.

FIG. 1 is a perspective view of an injection pen 11 according to an exemplary embodiment of the present invention. As shown, the injection pen 11 includes a pen upper body or housing 1, which houses a plurality of dose setting and injection components. The upper body 1 is connected to a cartridge housing 17, which houses a medication cartridge 18, as shown in FIGS. 1 and 3. The injection pen 11 may also include a lower pen cap (not shown) to cover the cartridge 18 and cartridge housing 17 when the injection pen 11 is not in use. As shown, the injection pen 11 includes a dose set knob 2 that includes a knob-like portion 4 that is rotated by a user to set a desired dose. The dose set knob 2 also includes a plurality of numerals, as shown in FIG. 2, corresponding to a number of dosage units that is visible through a window 13 provided on the upper body 1, as shown in FIG. 8A. A user rotates the dose set knob 2 until the desired dose is visible in the window 13. The upper pen body 1 may include an arrow or other indicator 14 to precisely indicate the set dose. Once the desired dose is set, a user presses the button 3 until the set dosage amount is completely injected.

Figure 4:
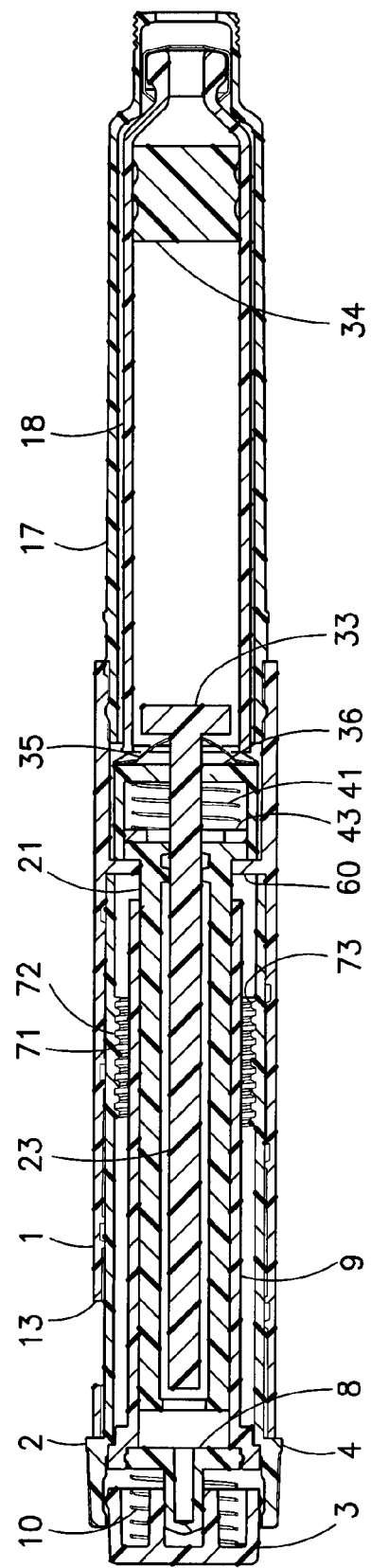
FIG. 4 is an enlarged elevational view in cross-section of the injection pen of FIG. 3 with the dose set knob.

A push button 3 is provided at a proximal end, closest to a user and farthest from a needle (not shown), of the upper pen body 1, as shown in FIG. 4. The push button 3 preferably comprises an annular bead or rim 5 that engages with a corresponding annular groove 6 provided on the internal surface of the knob-like portion 4 of the dose set knob 2. The annular rim/groove connection is preferably a friction fit that maintains the push button 3 in a biased position on the dose set knob 2 under the force of a button spring 10, but allows the push button 3 to be pushed into the dose set knob 2 for injecting a set dose. As shown in FIG. 4, the groove 6 in the knob-like portion 4 of the dose set knob 2 extends axially to allow the push button 3 to be pushed into the dose set knob 2 during an injection. The interior of the button 3 accommodates a setback bearing insert 8 that rests on an internal surface at a proximal end of the setback member 9. As shown in FIG. 4, the bearing insert 8 has an annular rim 12 received by an annular groove 13 (FIG. 5C) adjacent a proximal end 16 of the setback member 9. The push button 3 is designed to rotate freely on the setback bearing insert 8.

Figure 5A:
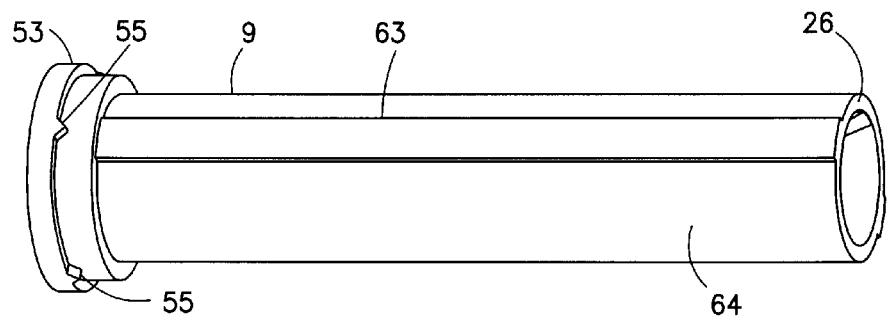
FIG. 5A is a perspective view of a setback member of the injection pen of FIG. 2.
Figure 5B:
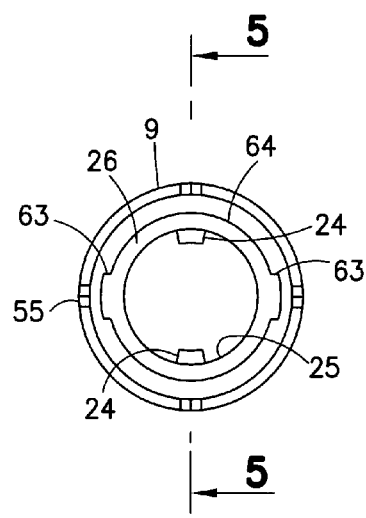
FIG. 5B is a distal end elevational view of the setback member of FIG. 5A.
Figure 5C:
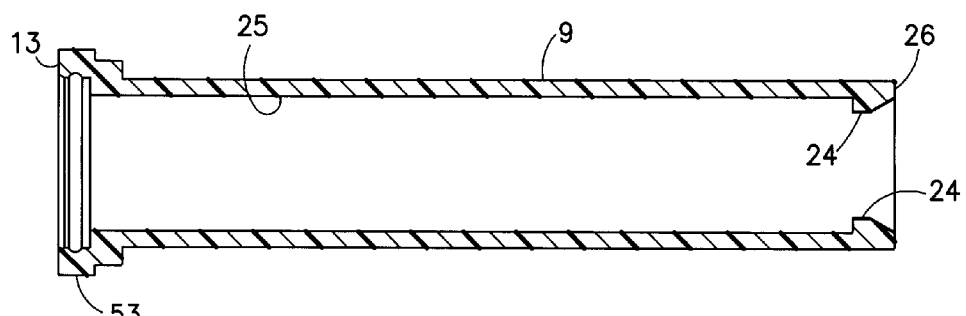
FIG. 5C is an elevational view in cross-section of the setback member of FIG. 5A.
Figure 6A:
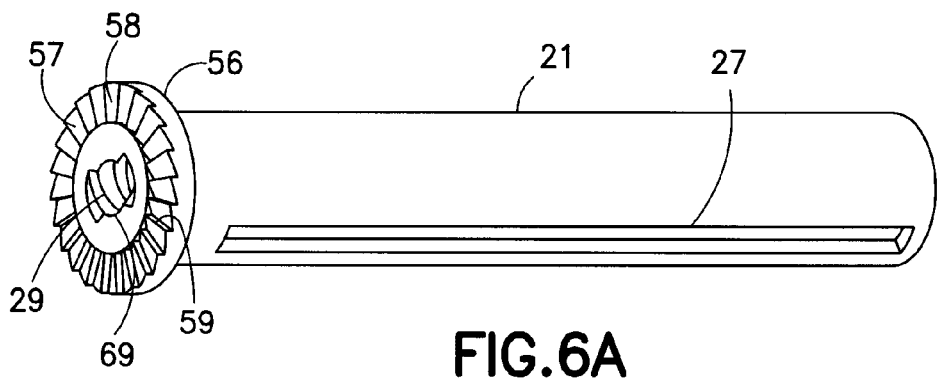
FIG. 6A is a perspective view of a driver of the injection pen of FIG. 2.
Figure 6B:
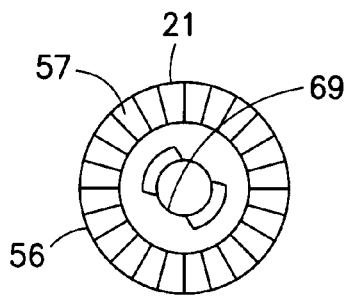
FIG. 6B is a distal end elevational view of the driver of FIG. 6A.
Figure 6C:
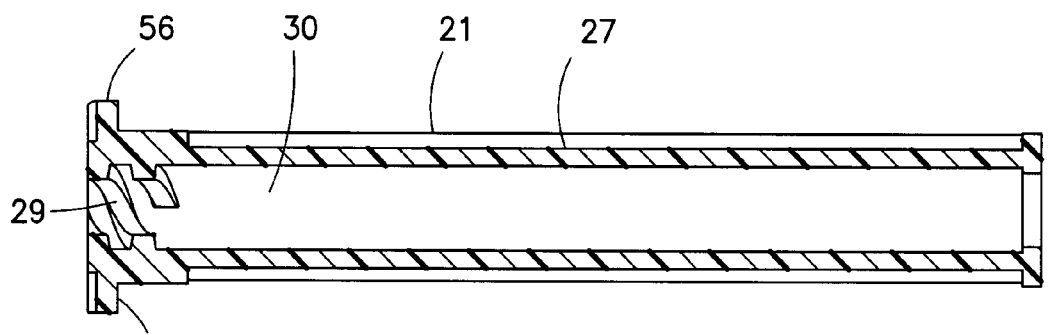
FIG. 6C is an elevational view in cross-section of the driver of FIG. 6A.

The setback member 9 is a cylindrical member, as shown in FIGS. 2 and 5A-5C, coaxial with and surrounded by the dose set knob 2. The setback member 9 is provided co-axially around a driver 21, as shown in FIGS. 3 and 4, that is rotatably fixed to the setback member 9 and axially movable relative to the setback member 9. The driver 21 co-axially surrounds a lead screw 23, as shown in FIGS. 3 and 4. The setback member 9 includes a set of keys 24 extending inwardly from an inner surface 25 at a distal end 26 that engage slots 27 extending axially on an outer surface 28 of the driver 21 to rotatably lock the driver 21 to the setback member 9. The driver 21 has threads 29 on a portion of an inner surface 30 thereof at a distal end of the driver 21, as shown in FIG. 6C. The driver 21 co-axially surrounds a lead screw 23, which includes a plurality of thread segments 31 disposed along substantially an entire axial length of the lead screw 23, as shown in FIGS. 2, 9A and 9B. The plurality of thread segments 31 are oppositely disposed with flattened portions 32 being disposed therebetween. A flange 33 is disposed at a distal end of the driver 23 to engage a stopper 34 disposed in the cartridge 18. The driver internal threads 29 are in threaded engagement with the external lead screw threads 31 provided on the lead screw 23. As described further below, due to its threaded engagement with the driver 21, the lead screw 23 is moved into the cartridge 18 during injection to press on a stopper 34 provided inside the cartridge 18 to expel a dose of medication. A wave clip 35, as shown in FIGS. 2 and 3, is provided between a distal end of a brake member 36 and a proximal end of the cartridge 18 to bias the cartridge 18 in a distal direction to substantially prevent movement of the cartridge 18 during injection, and thus ensure that an accurate dose is injected.

The brake member 36 is disposed in the pen upper body 1, as shown in FIGS. 3 and 4. The brake member 36 is a substantially cylindrical member having a substantially planar base 37 from which a wall 38 extends axially outwardly. An opening 39 in the base 37 receives the lead screw 23. A spring member 41 is disposed on an inner surface 42 of the base of the brake member 36. A ratchet disk 43 is disposed on the spring member 41. The ratchet disk 43 is preferably circular with an opening 44 therein to receive the lead screw 23. A pair of keys 45 extend outwardly from the ratchet disk 43 to engage the slots 40 in the brake member 36. The slots 40 substantially prevent rotational movement of the ratchet disk 43, while allowing axial movement of the ratchet disk 43. A plurality of teeth 46 extend upwardly from an upper surface 47 of the ratchet disk 43. Each tooth 46 has a sloped surface 48 forming an obtuse angle with the upper surface 47 and a stopping surface 49 disposed substantially perpendicularly to the upper surface 47.

To set a dose using the injection pen device of the first exemplary embodiment, a user rotates the knob-like portion 4 of the dose set knob 2 relative to the pen upper body 1. The outer surface of the dose set knob 2 includes a thread 50, as best shown in FIGS. 2 and 7A, that is in threaded engagement with a plurality of threads 51 provided on an internal surface 52 of the upper pen body 1, as shown in FIGS. 2 and 8C. Accordingly, as the dose set knob 2 is rotated relative to the upper pen body 1, the dose set knob 2 screws or advances a distance out of the upper pen body 1. The dose set knob 2 includes an annular shoulder or rim 52 on the interior surface thereof near the proximal end, as shown in FIGS. 7A and 7B. The annular shoulder 52 engages with an enlarged portion or head 53 of the setback member 9, as shown in FIGS. 2, 5A and 5C. The annular shoulder 52 of the dose set knob 2 preferably comprises a series of teeth or ridges 54 that engage with a plurality of similarly shaped teeth or ridges 55 provided on the enlarged head 53 of the setback member 9. During dose setting, the dose set knob 2 is free to rotate with respect to the setback member 9 in both a clockwise and counter-clockwise direction. As this occurs, the plurality of teeth or ridges 54 of the dose set knob 2 slip past the teeth 55 provided on the enlarged head portion 53 of the setback member 9, thus providing a tactile signal or clicking noise indicating the setting of a dose unit. As further described below, the dose set knob 2 is enabled to rotate relative to the setback member 9 during setting due to a one-way ratchet that prevents the setback member 9 from rotating together with the dose set knob 2 in the setting direction.

Rotation of the dose set knob 2 in the dose setting direction is not transferred to the setback member 9 due to the one-way ratchet between the driver 21 and the ratchet disk 43, as shown in FIG. 3. The setback member 9 near its distal end includes a pair of keys 24, as shown in FIGS. 2 and 5C. The pair of keys 24 engages a pair of slots 27 in the driver 21, as shown in FIGS. 2 and 6A. The keys 24 and slots 27 rotationally lock the setback member 9 and the driver 21 together while allowing for axial movement of the setback member 9. A flange 56 disposed at a distal end of the driver 21 has a plurality of teeth 57 disposed on a lower surface thereof. The driver teeth 57 have sloped surfaces 58 and stopping surfaces 59, as shown in FIG. 6A. The stopping surfaces 59 of the driver teeth 57 engage the stopping surfaces 49 of the ratchet disk teeth 46, thereby preventing rotation of the driver 21. The spring member 41 biases the ratchet disk 43 into engagement with the driver flange to facilitate preventing rotation of the driver 21. Accordingly, preventing the driver 21 from rotating also prevents the setback member 9 from rotating. As the dose set knob 2 is rotated out of the pen upper body 1 during dose setting, the engagement between the enlarged head portion 53 of the setback member 9 and the shoulder 52 of the dose set knob 2 causes the setback member 9 to move axially as the keys 24 slide within the driver slots 27. As noted above, the dose set knob teeth 54 slip past the setback member teeth 55 during dose setting to provide a clicking noise to indicate to the user that a dose is being set.

To correct a set dose that may have been set too high, the user rotates back the dose set knob 2 in the opposite direction. Rotation of the dose set knob 2 in this direction is not transferred to the setback member 9 due to the one-way ratchet between the driver 21 (to which the setback member 9 is rotationally fixed) and the ratchet disk 43, as shown in FIG. 3. The friction between the teeth 54 and 55 of the dose set knob 2 and the setback member 9 is not large enough to overcome the friction between the driver flange 56 and the spring-biased ratchet disk 43. Thus, the dose set knob 2 can be rotated back to correct a set dose without causing rotation of the setback member 9 in this direction, although the setback member 9 will move axially due to the engagement of the setback member keys 24 in the driver slots 27. Accordingly, the dose set knob teeth 54 slip past the setback member teeth 55, which is prevented from rotating, to provide a clicking noise during dialing back of the dose, just as during normal dose setting.

As the dose set knob 2 screws or advances axially out of the upper body 1 during the setting of a dose, the setback member 9 is also caused to move axially out of the body a corresponding distance. This axial movement is caused by the engagement between the annular shoulder 52 on the dose set knob 2 pushing against the enlarged head portion 53 of the setback member 9 during its movement out of the pen upper body 1. Once a desired dose is set, the user pushes the push button 3 that is coupled to the setback bearing insert 8 that is axially connected to the setback member 9. Under the force applied by the user pressing the push button 3, the setback member 9 is moved into a locking or meshing engagement with the dose set knob 2 via a meshing of the respective teeth or ridges 55 and 54 provided on the setback member 9 and the dose set knob 2, respectively. As the user continues to press the push button 3, the dose set knob 2 is caused to rotate and screw back down into the pen upper body 1 via the thread engagement between the thread 50 on the dose set knob 2 and the thread 51 in the pen upper body 1. Rotation of the dose set knob 2 is then transferred to the setback member 9 due to their locking or meshed engagement. The force of the user pressing the button 3 is enough to overcome the friction between the disk ratchet 43 and the driver flange 56, and as a result, the setback member 9 is enabled to rotate in this direction.

Rotation of the setback member 9, as allowed during injection, is then transferred to the driver 21, which is rotatably fixed to the setback member 9 via a key groove connection provided between the driver 21 and the setback member 9. As shown in FIGS. 5B and 5C, the internal surface 25 of the setback member 9 has inwardly extending keys 24 that engage axially extending slots 27 in the driver 21, as shown in shown in FIG. 3. The setback member 9 preferably includes two oppositely disposed keys 24 for engaging two oppositely disposed slots 27 in the driver 21. The setback member 9 moves axially relative to the driver 21 during dose setting and dose correcting, via the key 24 and slot 27 interconnection as shown in FIG. 3. The length of the slot 27 in the driver 21 can be configured to correspond to a maximum allowed dose to be injected in a single injection. The driver 21 is axially fixed with respect to the pen upper body 1 by a transverse wall 60. An upper surface 61 of the flange 56 abuts the transverse wall 60 of the pen upper body 1. The spring member 41 biases the driver flange 56 into contact with the transverse wall 60 through the ratchet disk 43.

As the setback member 9 rotates with the dose set knob 2 during injection, the driver 21 is rotated with the setback member 9. The sloped surfaces 58 and 46 of the driver teeth 57 and the ratchet disk teeth 46 engage such that the driver 21 rotates relative to the ratchet disk 43. The spring member 41 biases the ratchet disk 43 into contact with the driver flange 56, thereby generating a tactile signal and/or clicking noise as the driver teeth 57 slip over the ratchet disk teeth 46. The outwardly extending keys 45 of the ratchet disk 43 are received in the brake member slots 40, thereby preventing rotation of the ratchet disk 43.

As described above, the lead screw 23 includes a plurality of thread segments 31 that are in threaded engagement with threads 29 of the partially threaded driver 21, as shown in FIG. 3. Preferably, only a few thread segments are provided at a distal end of the driver 21 as shown in FIG. 6C. The lead screw 4 is held non-rotatable with respect to the upper pen body 1 by the opening 39 in the brake member 36. The opening 39 has a shape corresponding to the shape of the lead screw 4, which is flattened sides, such that the lead screw 4 is prevented from rotating relative to the brake member 36. The brake member 36 is prevented from rotating relative to the pen upper body 1 due to the engagement between the slots 40 in the brake member 36 and axially extending ribs 62 extending distally from the transverse wall 43, as shown in FIGS. 3, 8B and 8C. The rotation of the axially fixed driver 21 rotates the lead screw 23 through the threaded engagement therebetween, thereby driving the lead screw 23 distally into the cartridge 18. The axial movement of the lead screw 23 pushes the stopper 34 distally into the cartridge 18 to expel medicament stored therein.

Figure 10:
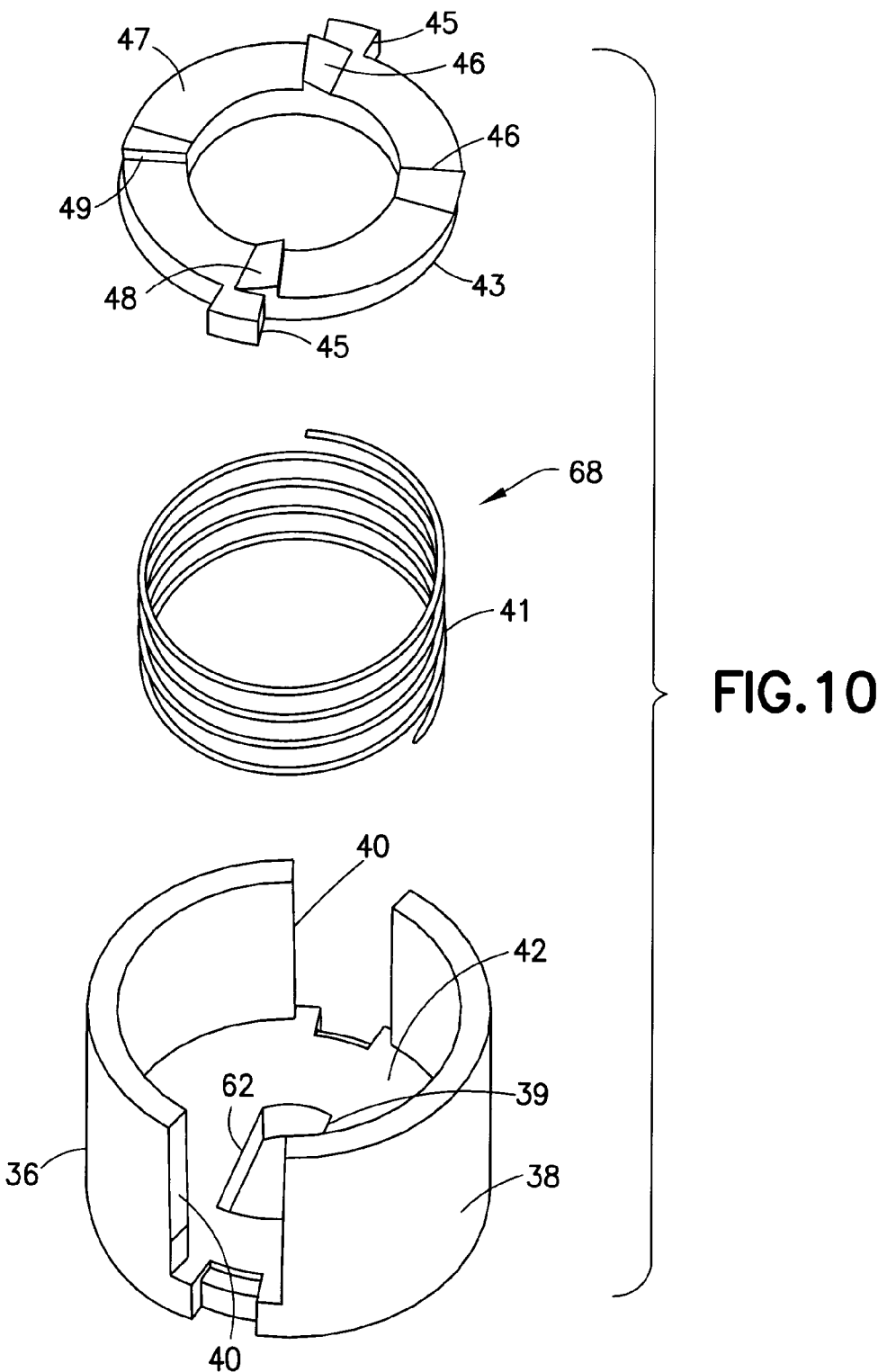
FIG. 10 is an exploded assembly view of a brake assembly of the injection pen of FIG. 2.
Figure 11A:
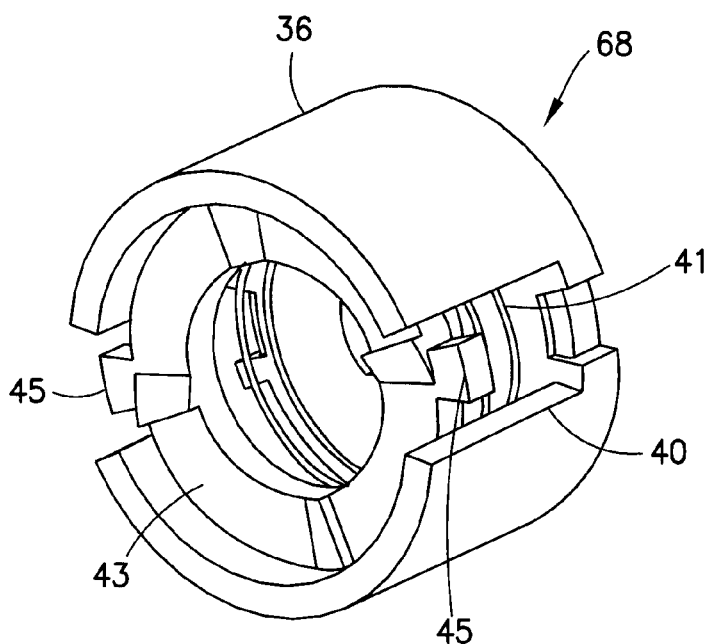
FIG. 11A is a perspective view of the brake assembly of FIG. 10.
Figure 11B:
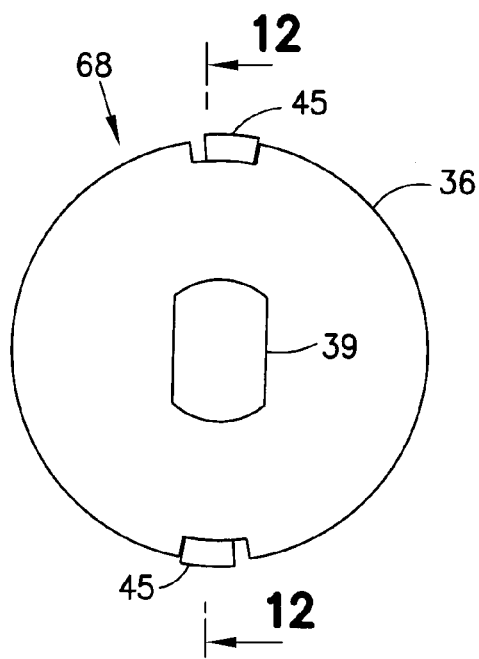
FIG. 11B is a distal end elevational view of the brake assembly of FIG. 11A.
Figure 11C:
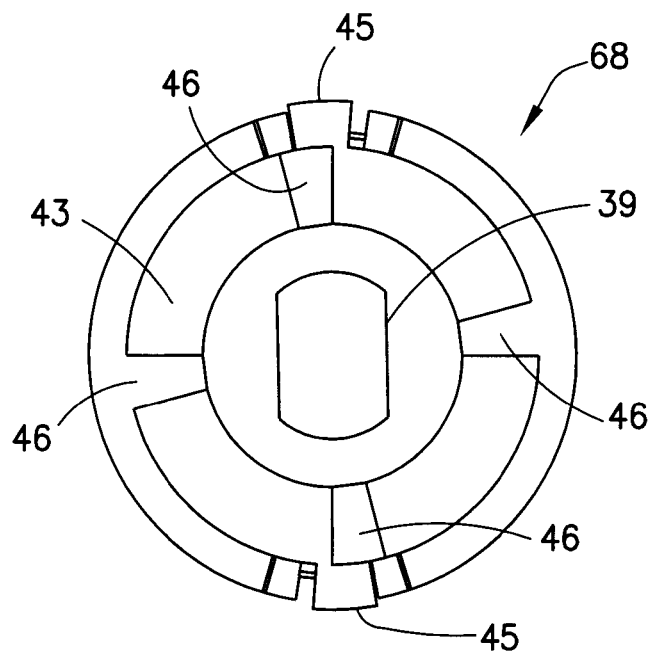
FIG. 11C is a proximal end elevational view of the brake assembly of FIG. 11A.
Figure 12:
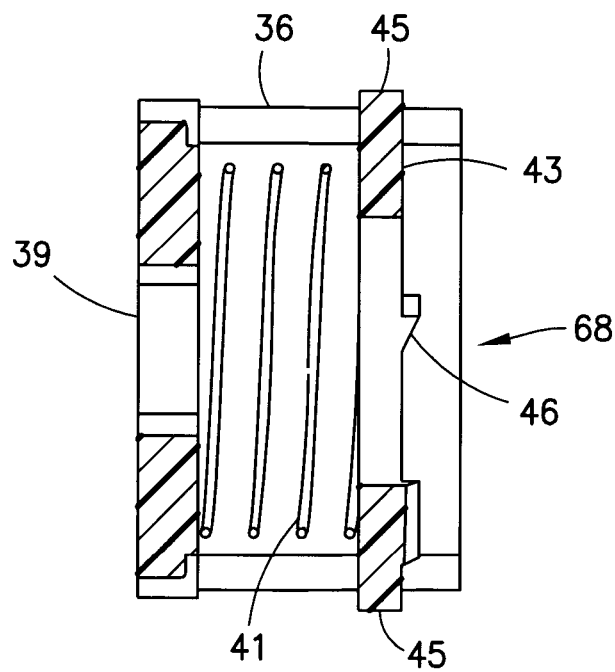
FIG. 12 is an elevational view in cross section of the brake assembly of FIG. 10.

During assembly, the driver 21 is inserted in the pen upper body 1 from the distal end. The brake assembly 68 includes the brake member 36, the spring member 41 and the ratchet disk 43, as shown in FIGS. 10-12. The brake assembly 68 is inserted in the pen upper body 1 from the distal end. The lead screw 23 is inserted through the opening 39 in the brake member 36 and through an opening 69 in the driver 21. The driver 21 is then rotated to draw the lead screw 23 proximally. The slots 40 in the brake member 36 rotationally fix the brake member 36 to the pen upper body 1. The flattened sides 62 of the brake member opening 39 receive the flattened portions 32 of the lead screw threads 31 to prevent rotation of the lead screw 23 and limit the lead screw to axial movement.

Because the lead screw 23 is non-rotatable with respect to the body 1, as the driver 21 is caused to rotate during injection, as described above due to its rotational coupling with the setback member 9, the lead screw 23 through its threaded engagement with the driver 21 is caused to move in the distal direction to press against the stopper 34 disposed in the medicament cartridge 18, thus expelling a liquid medication therefrom. The lead screw 23 is prevented from moving in the proximal direction because the driver 21 is rotatable in only a single direction (that which results in distal movement of the lead screw 23) due to the one-way ratchet between the driver 21 and the ratchet disk 43 of the brake member 36. Thus, accurate dosing can be ensured because the lead screw 23 maintains its engagement with the stopper 34 between injections. A mechanical advantage is preferably provided such that the dose set knob 2 moves further in the axial direction than the lead screw 23 during the injection, reducing the injection force that must be applied by the user. This is preferably accomplished by providing different pitches for the threaded connection between the dose set knob 2 and the pen upper body 1 and the threaded connection between the driver 21 and the lead screw 23. The ratio between the thread pitches can vary depending on the liquid medication and the expected dose volumes. For example, the pitch ratio can be 4.35:1 or 3.25:1, but is not limited thereto.

Figure 7C:
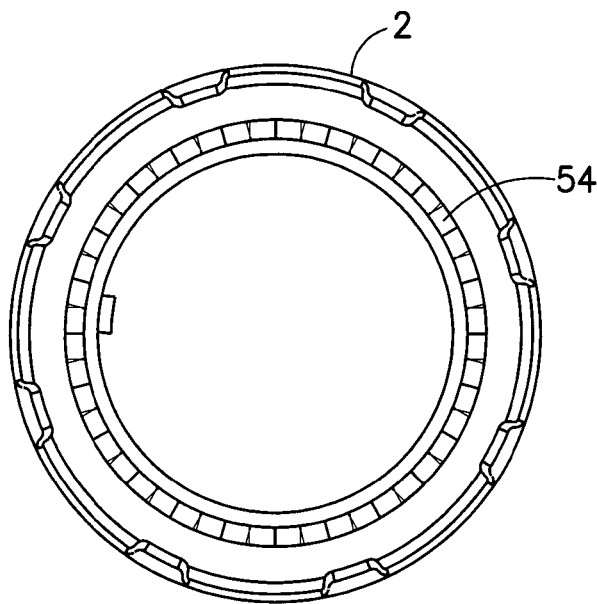
FIG. 7C is a proximal end elevational view of the dose set knob of FIG. 7A.

A dose stop member 71 (FIGS. 2 and 4) can be provided for last dose management, to prevent the setting of a dose that is larger than the remaining amount of medication in the cartridge 18. The dose stop member 71 is axially slidable but rotationally fixed with respect to the setback member 9 by being positioned between a pair of splines 63 provided on an outer surface 64 of the setback member 9, as shown in FIGS. 2, 5A and 5B. The dose stop member 71 is preferably a half-nut like element that is threaded on its outer surface with a plurality of threads 72. The dose stop member threads 72 are configured to engage with corresponding threads 65 provided on an inner surface 66 of the dose set knob 2, as shown in FIGS. 7A-7C. Initially, the dose stop member 71 is threadedly engaged with one or two of the proximal-most threads of threads 65 provided on the dose set knob 2. During dose setting, as the dose set knob 2 rotates relative to the setback member 9 and therefore also the dose stop member 71, the dose stop member 71 is caused to slide in the distal direction by a distance corresponding to the set dose due to its engagement with the threads 65 in the dose set knob 2.

Figure 7D:
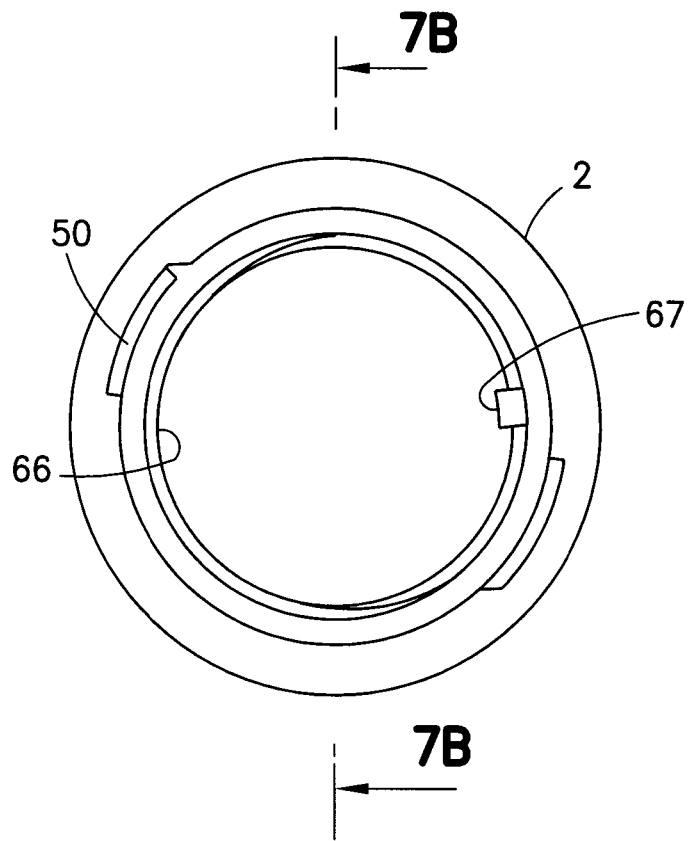
FIG. 7D is a distal end elevational view of the dose set knob of FIG. 7A.

During injection, because the setback member 9 and the dose set knob 2 are rotationally coupled as discussed above, the dose stop member 71 maintains its position relative to the threads 65 of the dose set knob 2. The dose stop member 71 moves in the distal direction during dose setting until a distal edge 72 (FIG. 4) of the dose stop member 71 abuts an inwardly directed key 67 provided on the inner surface 66 of the dose set knob 2, as shown in FIGS. 7B and 7D. In this position, the dose stop member 72 is prevented from further movement in the distal direction which also prevents further rotation of the dose set knob 2 to set an additional dose. In its final position, the dose stop member 71 is threadedly engaged with approximately two of the distal most threads of the threads 65 provided in the dose set knob 2. As shown in FIG. 7B, the total distance traveled by the dose stop member 71 from its initial position to its final position when it abuts key 67 provided on the dose set knob 2, is greater than the length of either of the thread portions provided on the dose stop member 71 and the dose set knob 2, respectively.

FIGS. 13-19D illustrate a second exemplary embodiment of an injection pen with similar functionality to the first exemplary embodiment. Like reference numerals have been included where the depicted components are substantially the same, and descriptions thereof are not repeated for brevity.

Figure 13:
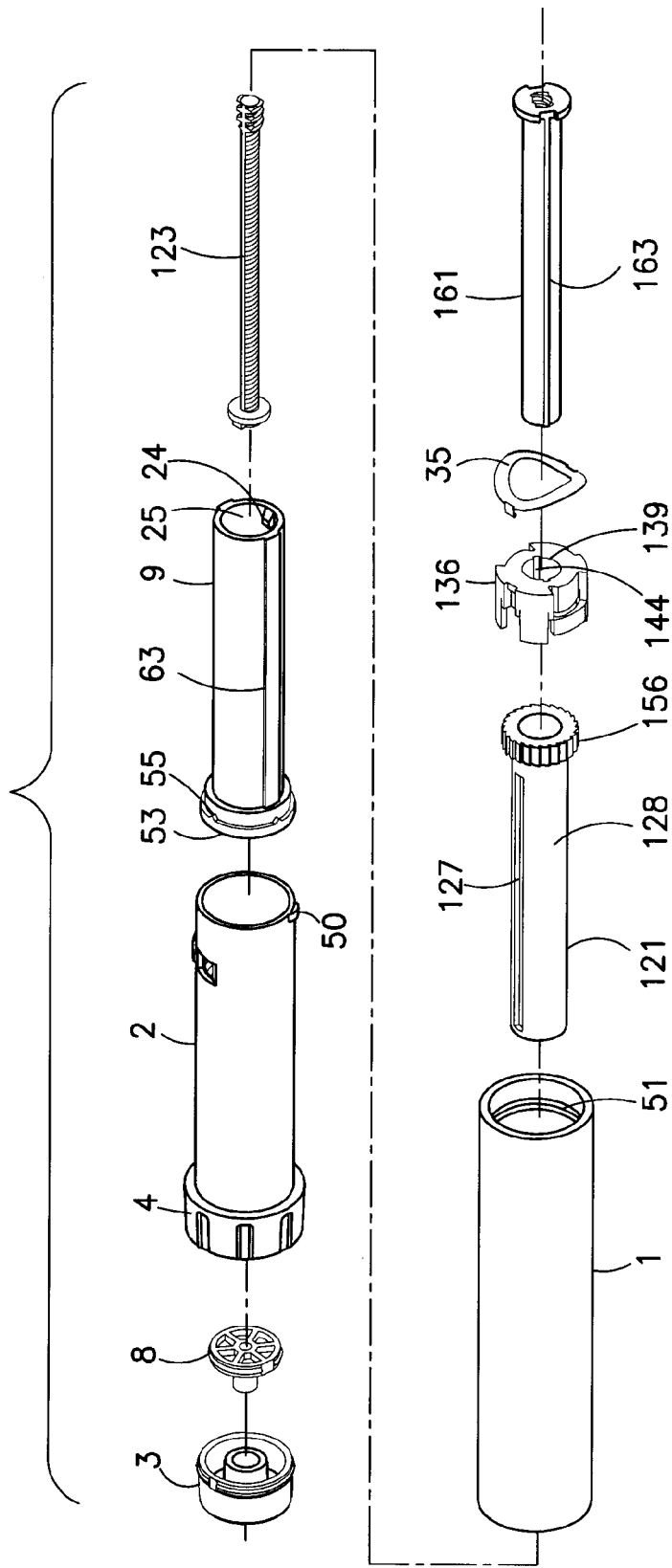
FIG. 13 is an exploded perspective view of an injection pen according to a second exemplary embodiment of the present invention.
Figure 14:
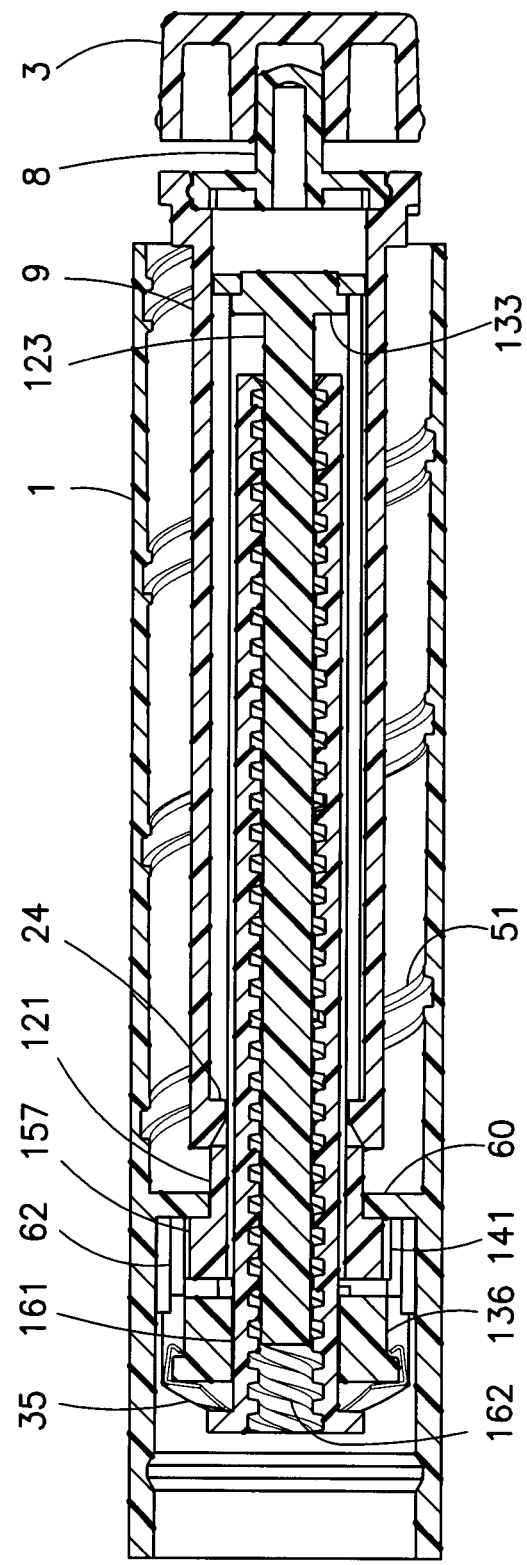
FIG. 14 is an elevational view in cross-section of the injection pen of FIG. 13 without a dose set knob for clarity.

The setback member 9 is a cylindrical member, as shown in FIG. 13, coaxial with and surrounded by the dose set knob 2. The setback member 9 is provided co-axially around a brake tower 121, as shown in FIGS. 13 and 14, that is rotatably fixed to the setback member 9. The setback member 9 is axially movable relative to the brake tower 121. The brake tower 121 co-axially surrounds a lead screw 123, as shown in FIGS. 13 and 14. The setback member 9 includes a set of keys 24 extending inwardly from an inner surface 25 at a distal end 26 that engage slots 127 extending axially on an outer surface 128 of the brake tower 121 to rotatably lock the brake tower 121 to the setback member 9. The brake tower 121 co-axially surrounds a piston rod 161, which is disposed between the brake tower 121 and the lead screw 123. The lead screw 123 is partially threaded, and has a plurality of thread segments 161 disposed along a portion of its axial length at a distal end 134 of the lead screw 123, as shown in FIGS. 16A and 16B. The plurality of thread segments 131 are oppositely disposed with flattened portions 132 being disposed therebetween. A flange 133 is disposed at a distal end of the driver 133 to engage the brake tower 121, as shown in FIGS. 14 and 16A-16C. The piston rod has internal threads 162 that preferably extend along its entire inner surface, as shown in FIGS. 18A-18C. The internal threads 162 of the piston rod 161 are in threaded engagement with the external lead screw threads 131 provided on the lead screw 123. As described further below, due to its threaded engagement with the brake tower 121, the lead screw 123 is moved into the cartridge 18 (FIG. 2) during an injection to press on a stopper 34 (FIG. 2) provided inside the cartridge 18 to expel a dose of medication. A wave clip 35, as shown in FIGS. 13-15, is provided between a distal end of a brake member 136 and a proximal end of the cartridge 18 to bias the cartridge 18 in a distal direction to substantially prevent movement of the cartridge 18 during injection, and thus ensuring an accurate dose is injected.

Figure 15:
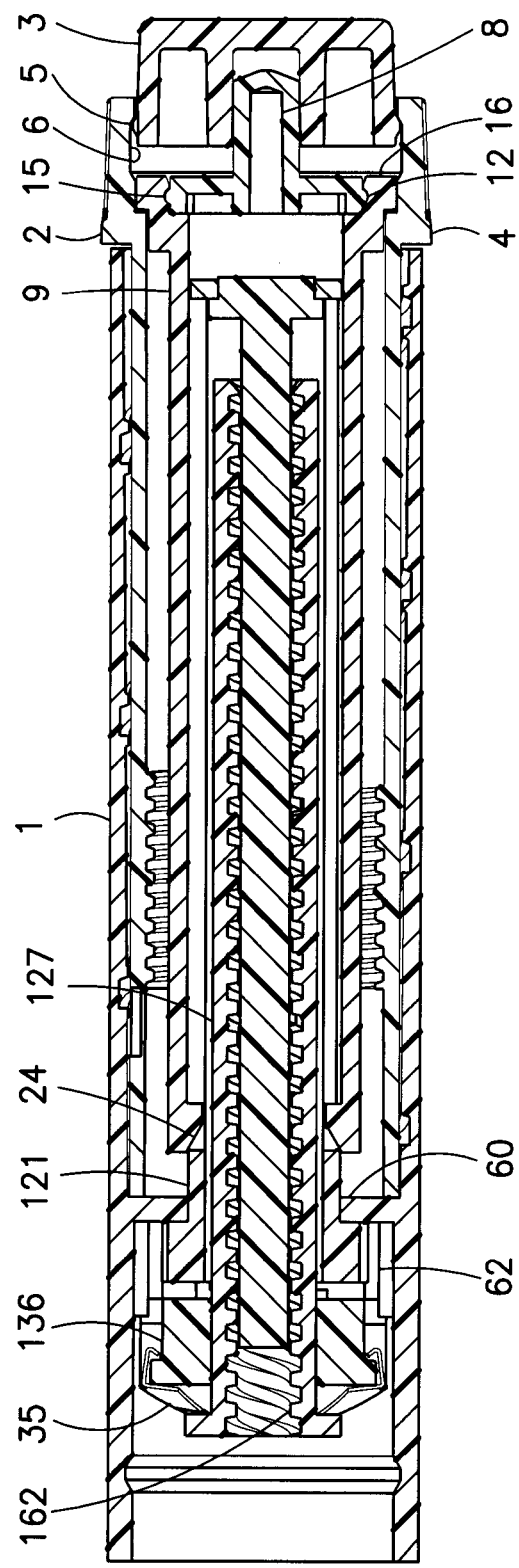
FIG. 15 is an elevational view in cross-section of the injection pen of FIG. 13.
Figure 16A:
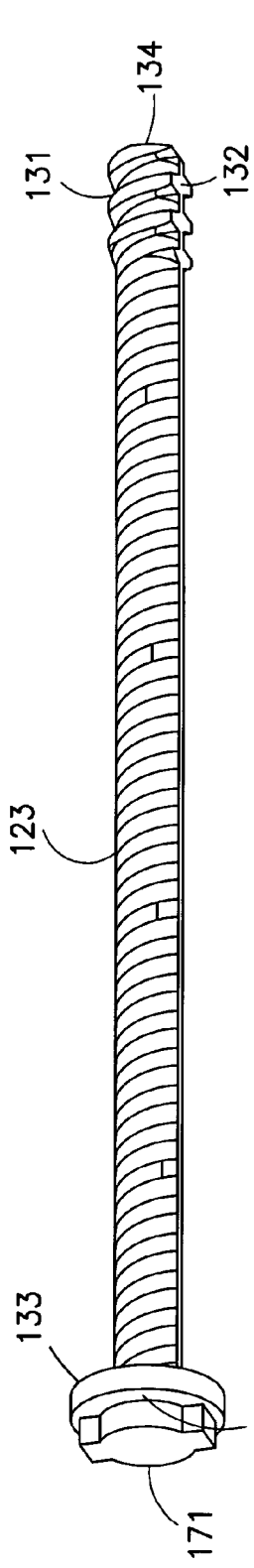
FIG. 16A is a perspective view of a lead screw of the injection pen of FIG. 12.
Figure 16B:
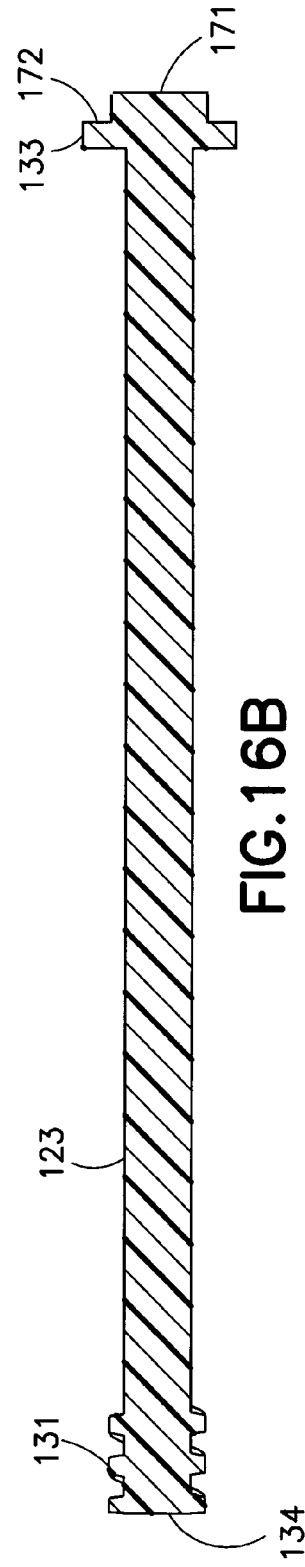
FIG. 16B is an elevational view in cross-section of the lead screw of FIG. 16A.
Figure 16C:
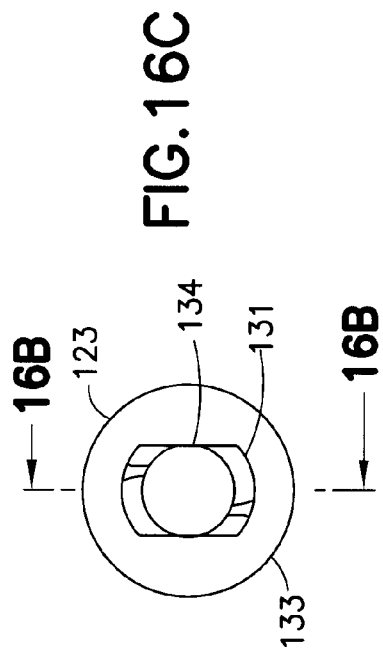
FIG. 16C is a distal end elevational view of the lead screw of FIG. 16A.

The brake member 136 is disposed in the pen upper body 1, as shown in FIGS. 14 and 15. The brake member 136 is a substantially cylindrical member having a substantially planar base 137 from which a wall 138 extends axially outwardly, as shown in FIGS. 19A-19E. An opening 139 in the base 37 receives the piston rod 161. A pair of substantially circumferentially extending flexible arms 141 are connected to the wall 138 of the brake member 136. Hooks 143 extend radially inwardly from free ends of the flexible arms 141. Each hook 143 has a sloped surface 148 forming an obtuse angle with the flexible arm 141 and a stopping surface 149 disposed substantially perpendicularly to the flexible arm 141. Slots 144 are formed in the opening to receive keys 163 extending radially along an outer surface 164 of the piston rod 161 (FIG. 18A). Slots 140 are formed in the wall 138 of the brake member 136 to receive the axial ribs 62 (FIG. 8B) of the pen upper body 1 to substantially prevent rotational movement of brake member 136 relative to the pen upper body 1. The hooks 143 of the flexible arms 141 engage radially extending teeth of the brake tower 121 to provide a one-way ratchet system therebetween.

To set a dose using the injection pen device of the second exemplary embodiment, the user rotates the knob-like portion 4 of the dose set knob 2 relative to the pen upper body 1. The outer surface of the dose set knob 2 includes a thread 50, as best shown in FIGS. 7A and 13, that is in threaded engagement with a plurality of threads 51 provided on an internal surface 52 of the upper pen body 1, as shown in FIGS. 2, 8C and 13. Accordingly, as the dose set knob 2 is rotated relative to the upper pen body 1, the dose set knob 2 screws or advances a distance out of the upper pen body 1. The annular shoulder 52 of the dose set knob 2 engages with the enlarged portion 53 of the setback member 9, as shown in FIG. 15. The annular shoulder 52 of the dose set knob 2 preferably comprises a series of teeth or ridges 54 that engage with a plurality of similarly shaped teeth or ridges 55 provided on the enlarged head 53 of the setback member 9. During dose setting, the dose set knob 2 is free to rotate with respect to the setback member 9 in both a clockwise and counter-clockwise direction. As this occurs, the plurality of teeth or ridges 54 of the dose set knob 2 slip past the teeth 55 provided on the enlarged head portion 53 of the setback member 9, thus providing a tactile signal or clicking noise indicating the setting of a dosage unit. As further described below, the dose set knob 2 is enabled to rotate relative to the setback member 9 during setting due to a one-way ratchet that prevents the setback member 9 from rotating together with the dose set knob 2 in the setting direction.

Figure 17A:
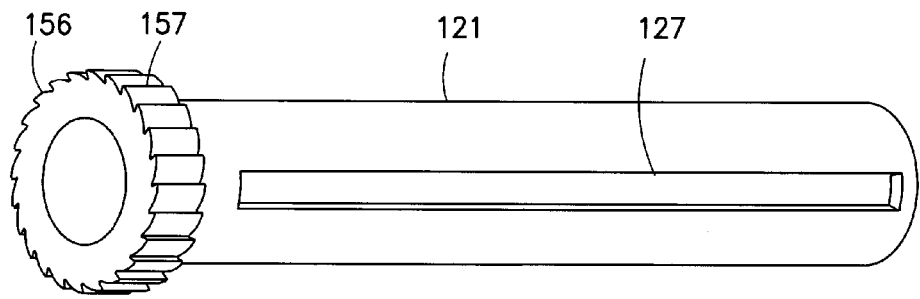
FIG. 17A is a perspective view of a brake tower of the injection pen of FIG. 12.
Figure 17B:
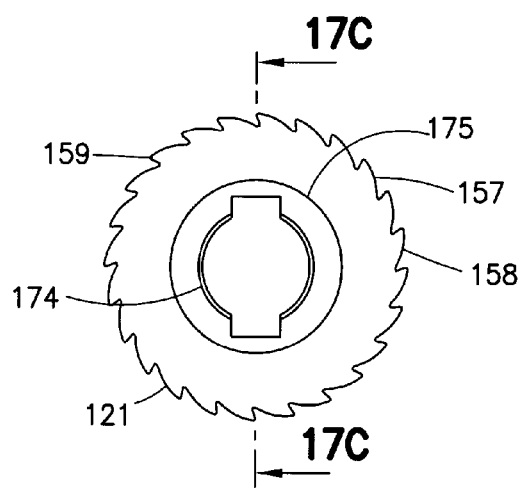
FIG. 17B is a distal end elevational view of the brake tower of FIG. 17A.

Rotation of the dose set knob 2 in the dose setting direction is not transferred to the setback member 9 due to the one-way ratchet between the brake tower 121 and the brake member 136, as shown in FIGS. 14 and 15. The setback member keys 24 engage the slots 127 in the brake tower 121. The keys 24 and slots 127 rotationally lock the setback member 9 and the brake tower 121 together. A flange 156 disposed at a distal end of the brake tower 121 has a plurality of teeth 157 extending radially outwardly therefrom. The brake tower teeth 157 have a sloped surface 158 and a stopping surface 159, as shown in FIG. 17B. The stopping surfaces 159 of the brake tower teeth 157 engage the stopping surfaces 149 of the brake member hooks 143, thereby preventing rotation of the brake tower 121. Accordingly, preventing the brake tower 121 from rotating prevents the setback member 9 from rotating. As the dose set knob 2 is rotated out of the pen upper body 1 during dose setting, the engagement between the enlarged head portion 53 of the setback member 9 and the shoulder 52 of the dose set knob 2 causes the setback member 9 to move axially as the keys 24 slide within the brake tower slots 127. The dose set knob teeth 54 slip past the setback member teeth 55 during dose setting to provide a clicking noise to indicate to the user that a dose is being set.

To correct a set dose that may have been set too high, the user rotates back the dose set knob 2 in the opposite direction. Rotation of the dose set knob 2 in this direction is not transferred to the setback member 9 due to the one-way ratchet between the brake tower 121 (to which the setback member 9 is rotationally fixed) and the brake member 136, as shown in FIGS. 14 and 15. The friction between the teeth 54 and 55 of the dose set knob 2 and the setback member 9 is not large enough to overcome the friction between the brake tower teeth 157 and the brake member hooks 141. Thus, the dose set knob 2 can be rotated back to correct a set dose without causing rotation of the setback member 9 in this direction, although the setback member 9 will move axially due to the engagement of the setback member keys 24 in the brake tower slots 127. Accordingly, the dose set knob teeth 54 slip past the setback member teeth 55, which is prevented from rotating, to provide a clicking noise during dialing back of the dose, just as during normal dose setting.

As the dose set knob 2 screws or advances axially out of the upper body 1 during the setting of a dose, the setback member 9 is also caused to move axially out of the body by a corresponding distance. This axial movement is caused by the engagement between the annular shoulder 52 on the dose set knob 2 pushing against the enlarged head portion 53 of the setback member 9 during its movement out of the pen upper body 1. Once a desired dose is set, the user pushes the push button 3 that is coupled to the setback bearing insert 8 that is axially connected to the setback member 9. A spring member 10 can be disposed between the push button 3 and the bearing insert 8, as shown in FIG. 2. Under the force applied by the user pressing the push button 3, the setback member 9 is moved into a locking or meshing engagement with the dose set knob 2 via a meshing of the respective teeth or ridges 55 and 54 provided on the setback member 9 and the dose set knob 2, respectively. As the user continues to press the push button 3, the dose set knob 2 is caused to rotate and move back distally into the pen upper body 1 via the thread engagement between the thread 50 on the dose set knob 2 and the thread 51 in the pen upper body 1. Rotation of the dose set knob 2 is then transferred to the setback member 9 due to their locking or meshed engagement. The force of the user pressing the button 3 is enough to overcome the friction between the brake member hooks 143 and the brake tower teeth 157, and as a result, the setback member 9 is enabled to rotate in this direction.

Rotation of the setback member 9, as allowed during injection, is then transferred to the brake tower 121, which is rotatably fixed to the setback member 9 via a key groove connection provided between the brake tower 121 and the setback member 9. As shown in FIGS. 5B and 5C, the internal surface 25 of the setback member 9 has inwardly extending keys 24 that engage axially extending slots 127 in the brake tower 121, as shown in shown in FIG. 15. The setback member 9 preferably includes two oppositely disposed keys 24 for engaging two oppositely disposed slots 127 in the brake tower 121. The setback member 9 moves axially relative to the brake tower 121 during dose setting and dose correcting, via the key 24 and slot 127 interconnection as shown in FIG. 15. The length of the slot 127 in the brake tower 121 can be configured to correspond to a maximum dose to be injected in a single injection. The brake tower 121 is axially fixed with respect to the pen upper body 1 by a transverse wall 60. An upper surface 118 of the flange 156 of the brake tower 121 abuts the transverse wall 60 of the pen upper body 1, as shown in FIGS. 14 and 15, to prevent axial movement of the brake tower 121 in the proximal direction. The cartridge 18 and the cartridge housing 17 threadably connected to the pen upper body 1 prevent axial movement of the brake tower 121 in the distal direction.

As the setback member 9 rotates with the dose set knob 2 during injection, the brake tower 121 is rotated with the setback member 9. The sloped surfaces 158 and 148 of the brake tower teeth 157 and the brake member hooks 143 engage and cause the brake tower 121 to rotate relative to the brake member 136. A tactile signal and/or clicking noise indicating dose delivery is generated as the brake tower teeth 157 slip over the brake member hooks 143. The slots 140 of the brake member 136 receive the ribs 62 of the pen upper body 1, thereby preventing rotation of the brake member 136.

Figure 17C:
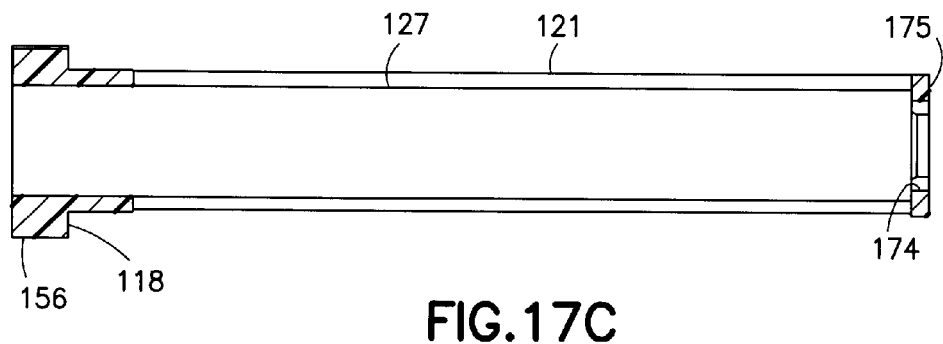
FIG. 17C is an elevational view in cross-section of the brake tower of FIG. 17A.
Figure 19A:
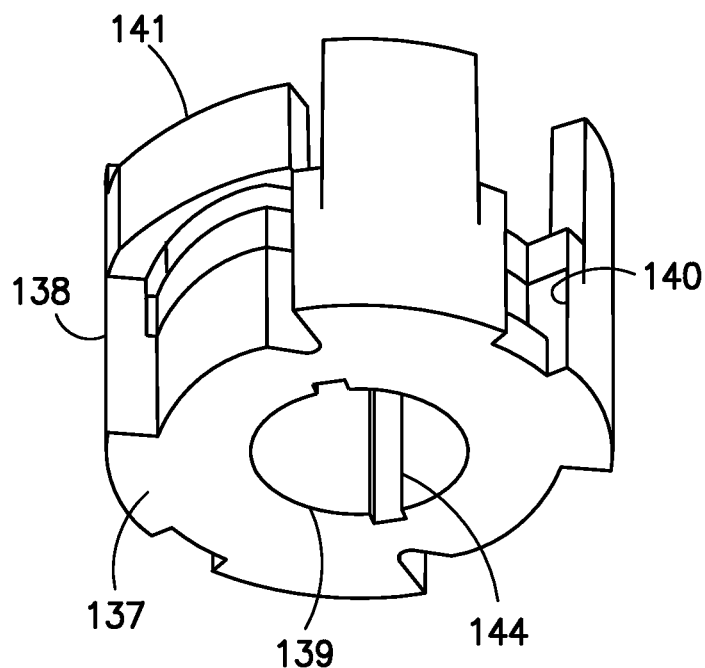
FIG. 19A is a distal end perspective view of a brake member of the injection pen of FIG. 12.
Figure 19B:
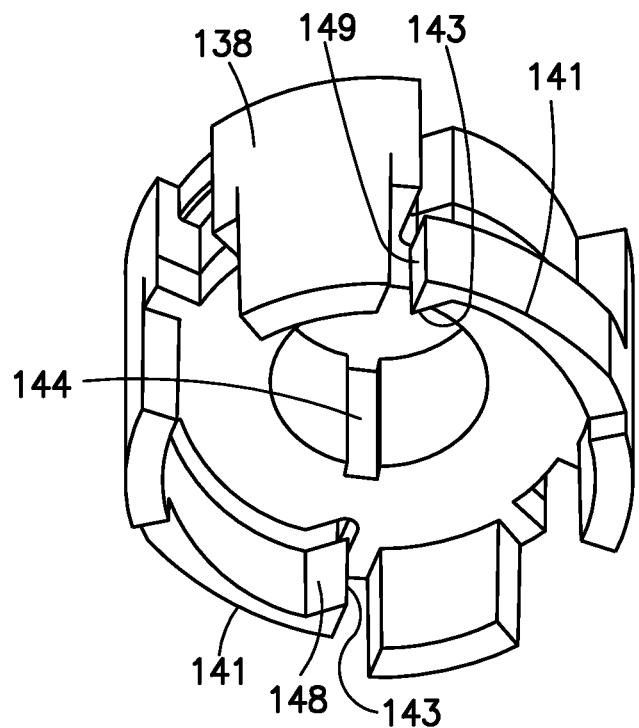
FIG. 19B is a proximal end perspective view of the brake member of FIG. 19A.
Figure 19C:
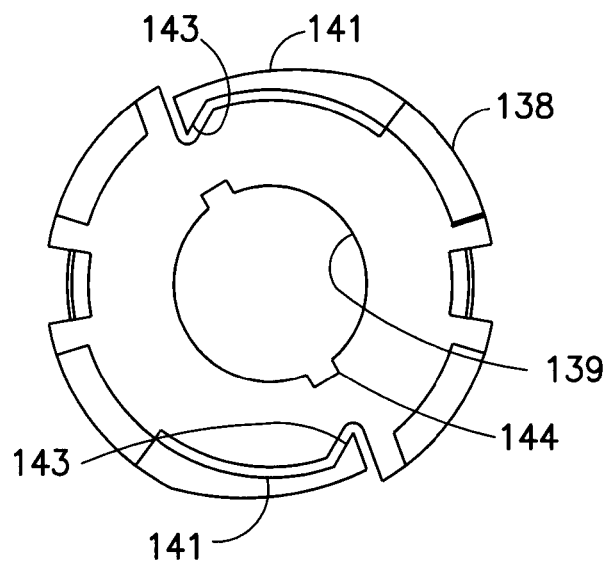
FIG. 19C is a proximal end elevational view of the brake member of FIG. 19A.
Figure 19D:
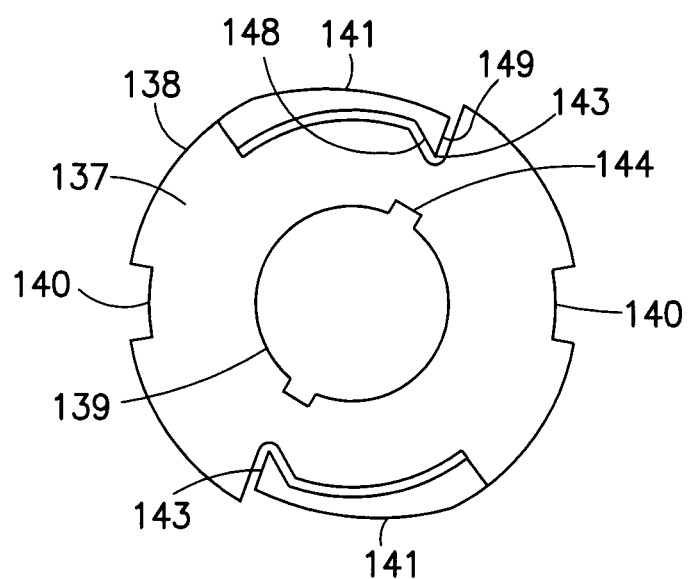
FIG. 19D is a distal end elevational view of the brake member of FIG. 19A.
Figure 19E:
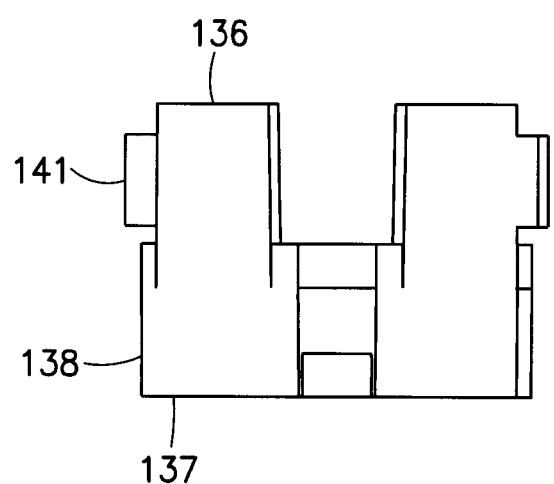
FIG. 19E is a side elevational view of the brake member of FIG. 19A.

As described above, the lead screw 123 includes a plurality of thread segments 131 that are in threaded engagement with threads 162 of the piston rod 161, as shown in FIGS. 14 and 15. Preferably, only a few thread segments are provided at a distal end of the lead screw 123, as shown in FIGS. 16A and 16B. The piston rod 161 is held non-rotatable with respect to the pen upper body 1 by the axially extending keys 163 received in the slots 144 in the opening 139 of the brake member 136. The keys 163 are received in the slots 144 to prevent rotation of the piston rod 161 in the brake member 136, which is prevented from rotating in the pen upper body 1 by the brake member slots 140 receiving the ribs 62 of the pen upper body 1. The rotation of the axially fixed brake tower 121 rotates the axially fixed lead screw 123 through the keyed connection therebetween. An axially extending key 171 extends from an upper surface 172 of the flange 133 of the lead screw 123, as shown in FIG. 16A. An opening 174 is formed in an inwardly extending flange 175 at a proximal end of the brake tower 121, as shown in FIGS. 17B and 17C. The brake tower opening 174 is shaped to correspond to the lead screw key 171, as shown in FIGS. 16A and 17C. The upper surface 172 of the lead screw flange 133 prevents proximal movement of the lead screw 123. Rotation of the brake tower 121 rotates the lead screw 123 through the keyed connection between the lead screw key 171 and the brake tower opening 174. The threaded engagement between the lead screw threads 131 and the internal threads 162 of the piston rod 161 drives the piston rod 161 distally into the cartridge 18. The axial movement of the piston rod 161 pushes the stopper 34 distally into the cartridge 18 to expel medicament stored therein.

Because the piston rod 161 is non-rotatable with respect to the pen upper body 1, as the lead screw 123 is caused to rotate during injection, as described above due to its rotational coupling with the brake tower 121, which is rotationally coupled to the setback member 9, the piston rod 161 through its threaded engagement with the lead screw 123 is caused to move in the distal direction to press against the stopper 34 disposed in the medicament cartridge 18, thus expelling liquid medication therefrom. The piston rod 161 is prevented from moving in the proximal direction because the lead screw 123 is rotatable in only a single direction (that which results in distal movement of the piston rod 161) due to the one-way ratchet between the brake member 136 and the brake tower 121. Thus, accurate dosing can be ensured because the piston rod 161 maintains its engagement with the stopper 34 between injections.

While the present invention has been shown and described with reference to particular illustrative embodiments, it is not to be restricted by such exemplary embodiments but only by the appended claims and their equivalents. It is to be appreciated that those skilled in the art can change or modify the exemplary embodiments without departing from the scope and spirit of the present invention.

The invention claimed is:

1. A medication injection pen, comprising:
a housing;
a dose set knob rotatable with respect to said housing;
a brake assembly disposed in said housing and having a ratchet member; and
a driver including at least one external tooth engaging said ratchet member,
wherein said engagement between said ratchet member and said at least one external tooth substantially prevents said driver from rotating with respect to said dose set knob during dose setting and dose correcting, and said engagement between said ratchet member and said at least one external tooth allows said driver to rotate with said dose set knob during an injection.

2. The medication injection pen according to claim 1, wherein
said at least one external tooth extends axially and said ratchet member extends axially.

3. The medication injection pen according to claim 1, wherein
said at least one external tooth extends radially and said ratchet member extends radially.

4. The medication injection pen according to claim 1, wherein
a spring member biases said ratchet member into said engagement with said at least one external tooth.

5. The medication injection pen according to claim 4, wherein
said spring member is integrally formed with said ratchet member.

6. The medication injection pen according to claim 1, wherein
said driver is axially fixed during said dose setting and said dose injecting.

7. A medication injection pen, comprising:
a housing;
a dose set knob rotatable with respect to said housing;
a brake assembly disposed in said housing and having a ratchet member;
a driver including at least one external tooth engaging said ratchet member; and
a lead screw axially movable by rotation of said driver to expel medication during an injection,
wherein said engagement between said ratchet member and said at least one external tooth substantially prevents said driver from rotating with respect to said dose set knob during dose setting and dose correcting, and said engagement between said ratchet member and said at least one external tooth allows said driver to rotate with said dose set knob during an injection.

8. The medication injection pen according to claim 7, wherein said brake assembly includes
a brake member;
said ratchet member disposed in said brake member; and
a spring member biasing said ratchet member toward said driver.

9. The medication injection pen according to claim 8, wherein
said ratchet member comprises a disk having a plurality of axially extending teeth.

10. The medication injection pen according to claim 9, wherein
keys extending outwardly from said disk are received by said brake member to prevent rotation of said disk.

11. The medication injection pen according to claim 8, wherein
said brake member receives axially extending ribs on an inner surface of said housing to substantially prevent rotation of said brake member.

12. The medication injection pen according to claim 1, wherein
said spring member is unitarily formed with said brake member as a single piece.

13. The medication injection pen according to claim 8, wherein
an opening in said brake member receives said lead screw, said opening preventing rotation of said lead screw.

14. The medication injection pen according to claim 7, wherein
said driver is partially threaded to rotate said lead screw.

15. A medication injection pen, comprising:
a housing;
a dose set knob rotatable with respect to said housing;
a brake assembly disposed in said housing and having a ratchet member;
a brake tower including at least one external tooth engaging said ratchet member;
a lead screw rotatable by rotation of said brake tower; and
a piston rod axially movable by rotation of said lead screw to expel medication during an injection,
wherein said engagement between said ratchet member and said at least one external tooth substantially prevents said lead screw from rotating with respect to said dose set knob during dose setting and dose correcting, and said engagement between said ratchet member and said at least one external tooth allows said lead screw to rotate with said dose set knob during an injection.

16. The medication injection pen according to claim 15, wherein said brake assembly includes
a brake member;
at least one flexible arm connected to said brake member; and
said ratchet member extending radially inwardly from said at least one flexible arm.

17. The medication injection pen according to claim 16, wherein
said brake member, said at least one flexible arm and said ratchet member are unitarily formed as a single piece.

18. The medication injection pen according to claim 16, wherein
keys extending outwardly from said piston rod are received by said brake member to prevent rotation of said piston rod.

19. The medication injection pen according to claim 16, wherein
said brake member receives axially extending ribs on an inner surface of said housing to substantially prevent rotation of said brake member.

20. The medication injection pen according to claim 15, wherein
said piston rod is internally threaded to engage external threads of said lead screw.

* * * * *